United States Patent [19]
Supplee et al.

[11] Patent Number: 5,948,943
[45] Date of Patent: Sep. 7, 1999

[54] PROCESS IMPROVEMENT TO PRODUCE LOW COLOR TRIMETHYLOLPROPANE

[75] Inventors: Carolyn Supplee; Rodolfo W. Laurel; George C. Seaman, all of Corpus Christi, Tex.

[73] Assignee: Celanese International Corporation, Dallas, Tex.

[21] Appl. No.: 08/951,607

[22] Filed: Oct. 16, 1997

[51] Int. Cl.$^6$ .................................................. C07C 27/26
[52] U.S. Cl. ........................ 568/854; 568/853; 210/639; 210/634
[58] Field of Search ................................... 568/853, 854; 210/634, 635, 511, 192, 639

[56] References Cited

U.S. PATENT DOCUMENTS 3,956,406  5/1976  Palmer et al. ........................... 260/637
5,603,835  2/1997  Cheung et al. ........................... 210/639

*Primary Examiner*—Shailendra Kumar
*Assistant Examiner*—Sreeni Padmanabhan
*Attorney, Agent, or Firm*—M. Susan Spiering

[57] ABSTRACT

Disclosed is a process for acquiring crude trimethylolpropane (TMP) of low reacted color. TMP is generally prepared by the condensation of n-butyraldehyde and formaldehyde in an alkali solution. The mixture is then concentrated and placed through an extractor. It has been found that a high concentration of low color TMP is present in the extractor and may by obtained by taking a slip stream of hot organic/water/TMP from the extractor and allowing the mixture to cool and phase separate. Upon separation of the phases, TMP generally having an acid wash color of about or less than 5 GU is recovered from the water phase. Disclosed is use of a single and multistage extractor.

19 Claims, No Drawings

PROCESS IMPROVEMENT TO PRODUCE LOW COLOR TRIMETHYLOLPROPANE

FIELD OF THE INVENTION

This invention relates to the production of trimethylolpropane (TMP) and more particular to obtaining low color crude TMP.

BACKGROUND OF THE INVENTION

This invention relates to a process for obtaining low reacted color (interchangeably referred to herein as "low color") crude trimethylolpropane (TMP).

Trimethylolpropane is produced by the condensation and cross Cannizzaro reactions of n-butyraldehyde and formaldehyde in the presence of a strong alkaline hydroxide, such as caustic solution. Removal of the TMP from the reactor solution can be carried out by the partition of the product between the aqueous solution and an organic solvent for the TMP, e.g., ethyl acetate, isobutanol, butyl acetate, and the like. The TMP is then removed from the organic layer, as for example by distillation. Another method for the removal of the TMP from the organic layer and the further removal of caustic from the TMP is to add a second solvent, one in which the TMP is insoluble, in an amount sufficient to separate the aqueous but not sufficient to separate out the TMP, remove the water layer, and then remove the first solvent by distillation. Typically the second solvent is a non-polar solvent, e.g., xylene. The TMP/second organic solvent mixture is allowed to settle and the separated TMP is removed by decantation. See Palmer et al., U.S. Pat. No. 3,956,406. These processes generally produce a product which has an acid-wash color of about 5–10 Gardner Units (GU) or phthalic anhydride color of about 100–300 APHA. Historically, the art has obtained low reacted color TMP by extracting, leaching, or further purifying color-causing impurities generated in the reaction to produce TMP.

Cheung in U.S. Pat. No. 5,603,835 discloses a process which extracts color-causing impurities generated in the reaction to produce TMP, the process comprising extracting purified final TMP with an organic solvent wherein the color bodies are soluble in, but not the TMP. This extraction is reported to result in greater than about 85% yield of TMP product having an acid-wash color of 3 or less Gardner Units. The phthalic anhydride color of the TMP product is also reported to be less than about 100 APHA.

Low color TMP is not analogous to high purity TMP. The acid wash color of TMP is determined by extracting TMP with an organic solvent, followed by washing the extract with sulfuric acid, and monitoring the reacted color, e.g., through a colorimeter, to obtain a Gardner Unit (GU) value. The purity of a TMP sample is generally increased/enhanced by (re)crystallization techniques, or the like. Recrystallization may remove salts generated by the reaction of formaldehyde and butyraldehyde, but not necessarily remove color body impurities found in the TMP product. Palmer (US '406) addressed enhanced sample purity of TMP, while Cheung (US '835) addressed enhanced color of TMP. Both US '406 and US '835 involve a type of extraction process for the TMP product desired.

Other processes have produced product having an acid-wash color of about 5–6 Gardner Units. However, for many applications it is desirable to obtain TMP product having as low an acid wash color, or other color analyses, as possible and this low color obtained in an economically efficient manner. Thus the art is continuously searching for methods to obtain low color TMP.

SUMMARY OF THE INVENTION

Disclosed is a process to obtain low color TMP in yields of at least 30%, having an acid wash color of less than about 5, and preferably less than about 3 GU. TMP is generally prepared by the condensation of n-butyraldehyde and formaldehyde in an alkali solution. The mixture is then placed through an extractor. It has been found that a high concentration of low color crude TMP is present in the extractor phase and may by obtained by taking a stream of hot solvent/water/TMP from the extractor and allowing the mixture, with or without additional water, to cool and phase separate. Upon separation of the phases TMP generally having an acid wash of less than 5 is recovered from the aqueous phase. Additional TMP or low color TMP recovery from the organic phase is optional. TMP obtained by the inventive process typically also has a phthalic anhydride color of less than about 100 APHA, most often between 0.1–50 APHA. Unlike the art, this inventive process involves obtaining crude TMP having low color, not solid end-product TMP which is to then be extracted, leached, or purified further via conventional methods. By crude TMP it is meant that TMP obtained after processing by this invention (i.e., after extraction and distillation).

DETAILED DESCRIPTION OF THE INVENTION

In accordance with this invention there is provided a process for obtaining TMP having an acid-wash and natural color of about or less than 5 (most typically less than 3) GU, and a phthalic anhydride color of less than about 100 APHA, most typically between 0–50 APHA. The process comprises recovering trimethylolpropane from a one phase solution of TMP in an organic solvent and water by allowing the solution to phase into at least two separate phases and recovering the trimethylolpropane from either the organic or the aqueous phase.

TMP is typically produced by the reaction of n-butyraldehyde and formaldehyde in the presence of a strong base, such as sodium hydroxide. A formate salt is produced as a co-product (sodium formate if sodium hydroxide is used) with the TMP. After neutralization of the excess base the TMP can be recovered from the aqueous solution containing the formate salt and neutralized base generally by solvent extraction, e.g., using solvents such as ethyl acetate, isobutanol, butyl acetate, and the like. The TMP is then separated from the organic solvent phase, for example by distillation.

It has now been found that this solvent extraction phase contains a high concentration of low color TMP which can be isolated easily and be rephased and both phases can be processed further. It has been found that at operating temperatures greater than about 150° F. (66° C.), TMP exists in one phase with the organic solvent and water in the extractor column. It was further discovered that the low color TMP could be obtained by separating the aqueous layer from the organic extractor stream at lower temperatures. The mixture is cooled to allow phase separation to occur. The low color TMP can then be isolated from the aqueous phase.

It was discovered that the addition of water to this organic/aqueous TMP stream increased the volume of aqueous phase and the quantity of low reacted color TMP available for recovery.

At a temperature greater than about 150° F. (66° C.), the TMP containing stream is in one phase with the organic solvent and other components present. TMP is typically cooled and separated from the solvent mixture in the extractor at process temperatures of about 32–212° F. (0–100° C.) and most preferably about 77–122° F. (25–50° C.). Organic solvents in the extractor include chemicals such as diethyl ether, methyl tert. butyl ether, dipropyl ether, ethyl tert. butyl ether, diethylene glycol dimethyl ether (DIGLYME), ethyl acetate, isobutanol, butyl acetate and esters of ethylene glycol or propylene glycol with $C_1$–$C_4$ acids and the like. The preferred solvents include diethyl ether, methyl tert. butyl ether and ethyl acetate, with most preferred being methyl tert. butyl ether and ethyl acetate. Generally, water is added to the TMP containing stream in an amount sufficient to enhance phasing and increase the volume of aqueous phase, generally this occurs at an addition of about 1–4% water based on total volume.

The extraction stream comprises primarily on a solvent-free basis TMP at a volume of about 77%, with trace quantities of EPDO, MCF, NPG, BMLF, DTMP, MELF, water, and about 3% of unidentifiable matter.

Abbreviations:
EPDO—2-ethyl-1,3-propane diol
MCF—monocyclic formal of TMP
NPG—neopentyl glycol
BMLF—bis(monolinear) formal of TMP
DTMP—ditrimethylolpropane
MELF—methyl(monolinear) formal of TMP After extraction, the hot TMP stream is cooled and water added if desired. Thereafter the organic phase proceeds through a recovery system and the aqueous phase proceeds through a finishing system. The TMP is recovered from the aqueous layer via conventional techniques.

In an embodiment wherein TMP is recovered from the aqueous phase, the decanted aqueous stream comprising TMP, sodium formate, water and impurities undergoes a four stage cycle. Column 1 involves use of the water—organic solvent stripper column wherein it is preferred to feed the stream at the top of the column under atmospheric pressure, at an overhead temperature of about 140–158° F. (60–70° C.), and a base temperature of about 248–266° F. (185–195° C.).

The residue stream of this first column (solvent stripper column) is directed to a second column identified as the vacuum flasher column or column 2. For column 2, the stream is preferably fed at the top of the column at a pressure of about 6 mm Hg and a preheater temperature of about 158–176° F. (70–80° C.), and overhead temperature of about 365–383° F. (185–195° C.), and a base temperature of about 401–419° F. (205–215° C.). This second column generally serves to remove heavy ends from the process (e.g., DTMP, BMLF).

Exiting column 2 as an overhead stream, is a stream of TMP (about 90% TMP) entering about the middle of column 3 which serves to concentrate further the TMP and remove any remaining heavy ends impurities present. Generally, the product is taken as an overhead with a vacuum pressure of about 1 mm Hg, overhead temperature of the column at about 284–320° F. (140–160° C.), and a base temperature of about 401–419° F. (205–215° C.). The heavy ends are removed as a residue from column 3 and the overhead contains primarily TMP for further processing.

TMP (about 94% TMP) enters column 4, a light ends removal (finishing) column for final processing and removal of remaining impurities. The final low color TMP is collected as a residue stream from column 4, with any light ends impurities (which include MCF, EPDO, NPG) being removed as an overhead stream. Typically, the TMP is taken as a residue stream with a vacuum pressure of about 1 mm Hg, an overhead temperature of about 284–320° F. (140–160° C.), and a base temperature of about 401–419° F. (200–215° C.).

Approximately 99% TMP was recovered from the aqueous layer of the extraction stream based on the present inventive process. The color of this final TMP product has been determined to be less than 5 GU, typically less than 3 GU.

In an alternate embodiment, the organic phase of the extraction stream may be processed as described herein to recover TMP. Approximately 98% TMP was recovered from the organic phase of the extraction stream. The recovery of crude low color TMP may be increased by adding additional water and/or by further lowering the temperature of either the extractor stream or organic phase.

Color testing results based on the above described processes follow:

TABLE I

Color Testing Results

|  | Aq. TMP. | Organic TMP#1 | Organic TMP#2 | CA TMP |
|---|---|---|---|---|
| AW color | 1.5 | 6.4 | 6.3 | 6–10 |
| NH (Pt/Co) | 2.2 | 3.4 | 4.7 | <5 |
| PA (AHPA) | 0 | 163 | 70 | 50–200 |
| PA (w/o Nitrogen Sparging) 1 | 1 | 1 | 1 | |

Commercially available (CA) TMP is that TMP obtained as a final product from traditional commercial manufacturing processes involving extraction, leaching, or further purification of the final TMP obtained.
Units for the Above: AW color = GU; PA (w/o $N_2$ sparging) = GU.
Abbreviations: Aq = aqueous; Organic = ethyl acetate organic phase; AW = acid wash; NC = natural color; PA = phthalic anhydride color; CA = commercially available.

The correspondence of Gardner units to APHA units is shown in Table II.

TABLE II

| Acid Wash Test Gardner Units | Phthalic Anhydride Reacted Color Test (APHA) |
|---|---|
| 0–1 | 0–40 |
| 4–5 | 70–100 |
| 6–7 | 170–200 |
| 8–10 | 200–300 |

The extraction can be carried out using either virgin or recycled plant solvent. Although either batch or continuous extraction may be used in the invention advantageously, the process is preferably carried out using a continuous extraction with internal recycle streams employed.

Variables which affect the recovery of the low color TMP include temperature, water content, amount of solvent, contact time, and number of stages. For example, recovery increases as temperature decreases or water addition increases.

A continuous, once-throughput extraction of the process of the instant invention can be carried out at from about 32° F. (0° C.) to about 212° F. (100° C.), preferably from about 77° F. (25° C.) to about 122° F. (50° C.). Low color TMP may be recovered in yields of up to about 100% from the aqueous phase, preferably from about 30% to about 50%.

This process describes recovering a portion of the TMP production as low reacted color TMP by a single stage phasing operation of the extraction steam into an organic phase and an aqueous phase. Options for increasing the volume of low reacted color TMP for recovery by further lowering temperature and/or further addition of water have been discussed previously. In addition, the extension of the single phase operation into a multi-stage phasing operation would significantly increase recovery. Countercurrent extraction of the extractor stream with water in a multi stage extractor would significantly increase the volume of low reacted color TMP for recovery. The countercurrent extractor could be designed so 90% or greater of the TMP is recovered as low reacted color product. In an embodiment of the multi stage extraction process, once cooled in the first extractor, the organic phase is forwarded to a second extractor where the second extractor is a multistage counter current extractor. This organic phase is contacted with water so as to extract additional low color TMP. If desired, some of the solvent could be removed, e.g., by evaporation, to reduce the organic feed rate to the multi stage extraction.

Acid washed (AW) color is a sulfuric acid wash color test. In this test, the color producing species are extracted from TMP with toluene and this toluene is reacted with sulfuric acid. The resultant color is measured on a colorimeter in Gardner units.

Phthalic anhydride (PA) is determined by reacting phthalic anhydride with TMP at elevated temperatures. The resultant polymer develops a color which is measured using a colorimeter in APHA units or Gardner units.

The natural color (NC) of TMP is the visual color of TMP. Typically it is a 10% by weight solution of TMP in water and is reported in APHA units.

Color Tests

The acid wash color of the TMP is determined using a sulfuric acid wash color test. In the test molten TMP is extracted with toluene or cyclohexane, followed by washing the extract with sulfuric acid. The reacted color is monitored through a colorimeter in Gardner Units.

a. Reference standards for color tests.

In performing color tests, a Hunter's Lab Tristimulus Colorimeter (ColorQuest # C4188) and software (#CMR-884) is used. ASTM liquid standards are used for calibration according to ASTM Method D 1544-80.

b. Cell Sizes

Color is shown to be dependent on cell sizes. A cell of 10-mm cuvette was used for color analysis.

c. Shaking

Color depends on the intensity of shaking the toluene extract with acid. Vigorous shaking is needed to ensure sufficient mixing between phases.

1. Add 20 g of TMP (to 0.1 g accuracy, crystalline or molten) to a 200 ml tared beaker. Add 80 g of reagent grade toluene (acid wash color of about 1 Gardner Unit).
2. Heat the solution with rapid agitation at 60° C. for 5 minutes. Use a magnetic stirring bar. Start timing at 60° C. once all the TMP melts.
3. Charge 75 ml (+/−1 ml) of the toluene layer to a 250 ml separatory funnel (decant or pipette). Add 25 ml (+/−1 ml) of concentrated sulfuric acid to the separatory funnel using a graduated cylinder. Shake the separatory funnel vigorously for 30 seconds, being sure that different phases mix thoroughly. Allow 4 minutes for the solution to phase out. The solution should show a temperature of about 45+/−2° C. Decant the acid layer (bottom).
4. Add a sufficient amount of the acid layer to fill a 10-mm *cuvette. Record color by means of a Hunter Lab Tristimulus Colorimeter. Data are noted to the nearest number in Gardner Units by using a special program, ColorQuest #C4188. This software converts chromaticity coordinates from the spectral transmittance data to Gardner Units. The calorimeter is calibrated by using ASTM solution standards (e.g. $K_2PtCl_6$) and color-disks.

* A Gardner tube and a comparator can be used to replace the colorimeter.

PA Color Test

This method of test describes a procedure for measuring the intensity of color developed when treating a sample with phthalic anhydride at a reaction temperature of 200° C. and a reaction time of 30 minutes.

Apparatus

1. Gardner/Hellige Varnish color comparator.
2. 10 mm *Gardner tube.
3. Wax or paraffin bath—a stirred, constant temperature wax bath capable of controlling efficiently the temperature at 200° C.±5° C.
4. Vibrating mixer.
5. Timer.

Reagents

Phthalic Anhydride, (99%).

Note: The quality of the phthalic anhydride can affect the color reaction. Aldrich brand phthalic anhydride is recommended.

Procedure

1. Place a 3.00 g sample in a test tube and add 3.00 g of the phthalic anhydride reagent. Loosely seal the tube with a cork stopper.
2. Suspend the tube in a wax bath maintained at 200±5° C. Set the timer for 30 minutes. Allow the test tube to remain in the wax bath until the solution melts and becomes clear (approximately 10 minutes). At this point, while wearing gloves remove the sample from the bath and wipe off the excess wax. Immediately place the test tube on the vibrating mixer and allow to stir for 20 seconds or until the sample is thoroughly mixed. Repeat the procedure for all samples.
3. After mixing, place the tube in the wax bath until the 30 minutes reaction time is completed. At the end of the reaction time remove the samples and wipe off the excess wax.
4. Allow the samples to cool to room temperature for 30 minutes.
5. Wipe the outside of the sample tubes to remove any material remaining from the sample preparation or reaction.
6. Read the color of the sample by inserting the sample tube into the color comparator apparatus and matching the color of the sample with one of the reference colors. *

* Replacing the color comparator with a Bausch and Lomb Spectronic 20 according to Cheung et al. yields APHA valves.

Natural Color Test (Pt/Co)

Apparatus: 1) HunterLab Tristimulus Colorimeter (ColorQuest) and computer. 2) Colorimeter cells, 20 mm path length Reagents and Materials 1. Type I deionized water for use as an instrument blank.
2. Black card to set the zero transmittance for the instrument.
3. Cobalt Platinum Color Standard.

Procedure

1. Initially standardize the equipment (i.e. calorimeter).
2. Prepare TMP for color analysis as follows:

TMP (10% solution)

1. Pour 10 mL of the hot TMP into a 100 mL graduated cylinder with 90 mL of warm water in it.
2. Stopper the cylinder and shake the sample until a homogeneous solution is formed.
3. Analyze the sample in the calorimeter.

The following non-limiting examples are provided to illustrate this invention further. All proportions are by weight unless otherwise indicated.

EXAMPLES

Example 1

The reacted color of purified TMP was reduced by the following process. 17,000 g of a 30% crude TMP, 60% ethyl acetate, and 10% H₂O solution at 149° F. (65° C.) was allowed to cool to 77° F. (25° C.). Upon cooling to room temperature, the solution phased into two layers. The aqueous layer was separated from the organic layer at 77° F. (25° C.). The TMP from either layer was then recovered by the following process. The solvent was removed via roto-evaporation at 158° F. (70° C.) and 1 mm Hg. Pure TMP (>98%) was obtained as an overhead product via batch vacuum distillation at 320° F. (160° C.) and 1 mm Hg. The TMP recovered from the aqueous layer had an acid wash color of 5 or less Gardner units. Whereas, the TMP obtained from the organic layer had an acid wash color of 10 or less Gardner units.

TABLE III

Composition of TMP Layers Separated at 77° F. (25° C.).

|  | EtOAc | TMP | MELF | BMLF | MCF | Unknowns | H₂O |
|---|---|---|---|---|---|---|---|
| aqueous layer | 15.8 | 31.0 | 0.2 | 0.6 | N.D. | 2.0 | 50.4 |
| organic layer | 90.3 | 4.3 | 0.1 | 0.2 | N.D. | 0.4 | 4.7 |

Example 2

TMP with a significantly lower acid washed color was obtained under the same process separation conditions stated in Example 1 except that a two column continuous purification system was used.

After solvent removal via roto-evaporation, the crude TMP from the aqueous and organic layer (90% or 70%, respectively) was purified first by removing the heavy ends, then the light ends via vacuum distillation. TMP was obtained as a residue stream for both layers.

The heavy end impurities (BMCF, DTMP) were removed using a 35-tray 2-inch inside diameter jacketed Oldershaw column. The column was fitted with a 300 mL reboiler. Thermal wells were placed in the reboiler, at tray 10, tray 25 and tray 35. Crude TMP was fed to the column at 4 grams/minute at tray 10. Heavy ends (BMLF, DTMP) were removed from the base of the column. The overhead stream containing 94% TMP and light end impurities (MCF, EPDO, NPG) was then fed into a 35-tray 2-inch inside diameter jacketed Oldershaw column fitted with 300 mL reboiler at 4 g/minute. Thermal wells were placed in the reboiler, tray 10, tray 25 and tray 35. Light ends were removed in the overhead stream and pure TMP was obtained out of the base.

TABLE IV

Composition and Color Analysis for TMP Recovered From the Aquous and Organic Phases

|  | TMP | Unknowns | H₂O | AW* | PA* |
|---|---|---|---|---|---|
| aqueous layer | 99.84 | 0.09 | 0.07 | 1 | <1 |
| organic layer | 99.27 | 0.66 | 0.07 | 7 | 2 |

*GU

Example 3

TMP was obtained by adding distilled and deionized water (2% by weight) to the organic extractor stream at 104° F. (40° C.). The mixture was phased at 104° F. (40° C.) and the resulting layers processed according to Example 2.

TABLE V

Composition and Color Analysis for TMP Recovered From the Aquous and Organic Phases With Additional Water at 104° F. (40° C.)

|  | TMP | unknowns | H₂O | AW[1] | PA[1] |
|---|---|---|---|---|---|
| aqueous layer | 99.66 | 0.16 | 0.18 | 1.5 | 1 |
| organic layer | 98.64 | 1.09* | 0.27 | 6.4 | 1 |

*unknowns include trace amounts of MCF and MELF
[1]= GU

The following table illustrates color analyses from TMP obtained by various manufacturers, all of whom produce the TMP by similar conventional methods.

TABLE VI

|  | AW(GU) | PA(APHA) | Natural Color (GU) |
|---|---|---|---|
| TMP Color Analysis For Various Manufacturers | | | |
| Competitor | | | |
| A | 4–8 | 50–90 | <5 |
| B | 10 | — | <5 |
| C | 6 | — | <5 |
| Lab Results from TMP processed in accordance with the present invention: | | | |
| Aq. Phase | 1–2 | <1 | 2.2 |
| EtAc* Phase | 6–7 | 70–160 | 3.4–4.7 |
| Sample Prepared by Conventional Method: | 8–9 | 530 | 1 |

*EtAc = ethyl acetate

What is claimed is:

1. A process for obtaining low reacted color trimethylolpropane (TMP) comprising recovering crude trimethylolpropane from a heated one phase solution of trimethylolpropane in an organic solvent and water, allowing the solution to cool and separate into at least two phases, and recovering the trimethylolpropane from the aqueous phase.

2. The process of claim 1 wherein the recovered TMP has an acid wash color of about 5 GU or less.

3. The process of claim 2 wherein the recovered TMP obtained has an acid wash color of 3 or less Gardner Units and a phthalic anhydride color of 70 or less APHA.

4. The process of claim 3 wherein the recovered TMP has an acid wash color of 1 or less Gardner Units and a phthalic anhydride color of 50 or less APHA.

5. The process of claim 1 wherein the recovered TMP has a phthalic anhydride color of less than 5 GU, and a natural color of less than 100 APHA.

6. The process of claim 1 wherein the organic solvent is selected from diethyl ether, methyl tert. butyl ether, dipropyl ether, ethyl tert. butyl ether, diethylene glycol dimethyl ether, ethyl acetate, butyl acetate, isobutanol and esters of ethylene glycol or propylene glycol with $C_1$–$C_4$ acids.

7. The process of claim 6 wherein the organic solvent is ethyl acetate, diethyl ether, or methyl tert. butyl ether.

8. The process of claim 7 wherein the solvent is ethyl acetate.

9. The process of claim 1 wherein the TMP is isolated from an aqueous phase.

10. The process of claim 1 wherein the hot TMP/organic/water phase is cooled and separated at between about 32–212° F. (0–100° C.).

11. The process of claim 10 wherein the hot TMP/organic/water phase is cooled and separated at between about 32–176° F. (0–80° C.).

12. The process of claim 11 wherein the TMP/organic/water phase is cooled and separated at about 77–122° F. (25–50° C.).

13. The process of claim 1 wherein the TMP is isolated from an organic phase.

14. The process of claim 1 wherein water is added to the organic phase in an amount sufficient to ensure phasing.

15. The process of claim 14 wherein about 1–4 wt % water is added to the organic phase.

16. The process of claim 1 wherein a one stage extractor is employed to phase the TMP/organic/water mixture.

17. The process of claim 1 wherein a multistage extractor is employed to phase the TMP/organic/water mixture.

18. The process of claim 1 wherein at least one single stage extractor and one multistage extractor is employed to phase the TMP/organic/water mixture.

19. The process of claims 18 wherein some of the organic solvent is removed prior to entering the multistage extractor.

* * * * *